US012694632B2

(12) United States Patent
Segev et al.

(10) Patent No.: US 12,694,632 B2
(45) Date of Patent: Jul. 28, 2026

(54) AUTOMATIC EDITING OF ELECTROANATOMICAL MAPS

(71) Applicant: BIOSENSE WEBSTER (ISRAEL) LTD., Yokneam (IL)

(72) Inventors: Meytal Segev, Haifa (IL); Fady Massarwa, Baka Al Gharbiyya (IL); Sigal Altman, Ramat Hashofet (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 707 days.

(21) Appl. No.: 18/084,787

(22) Filed: Dec. 20, 2022

(65) Prior Publication Data

US 2024/0203079 A1    Jun. 20, 2024

(51) Int. Cl.
| | |
|---|---|
| *A61B 5/367* | (2021.01) |
| *A61B 5/00* | (2006.01) |
| *A61B 5/339* | (2021.01) |
| *G06T 17/20* | (2006.01) |
| *G06T 19/20* | (2011.01) |

(52) U.S. Cl.
CPC .............. *G06T 19/20* (2013.01); *A61B 5/339* (2021.01); *A61B 5/367* (2021.01); *A61B 5/6852* (2013.01); *G06T 17/205* (2013.01); *G06T 2210/41* (2013.01); *G06T 2219/2012* (2013.01); *G06T 2219/2021* (2013.01)

(58) Field of Classification Search
CPC ......... A61B 5/367; A61B 5/339; A61B 5/343
See application file for complete search history.

(56) References Cited

U.S. PATENT DOCUMENTS

| | | | |
|---|---|---|---|
| 5,391,199 | A | 2/1995 | Ben-Haim |
| 5,443,489 | A | 8/1995 | Ben Haim |
| 5,558,091 | A | 9/1996 | Acker |
| 6,172,499 | B1 | 1/2001 | Ashe |
| 6,239,724 | B1 | 5/2001 | Doron |
| 6,332,089 | B1 | 12/2001 | Acker |
| 6,484,118 | B1 | 11/2002 | Govari |
| 6,618,612 | B1 | 9/2003 | Acker |

(Continued)

FOREIGN PATENT DOCUMENTS

EP        3015060 A1      5/2016

OTHER PUBLICATIONS

International Search Report for Corresponding PCT/IB2023/061780 dated Mar. 25, 2024.

*Primary Examiner* — George R Evanisko
(74) *Attorney, Agent, or Firm* — Clayton, McKay & Bailey, PC

(57) ABSTRACT

A method for mapping includes computing an initial three-dimensional (3D) form representing an inner surface of a cavity within a body of a living subject and receiving physiological data measured at multiple points distributed over the inner surface of the cavity. For each area among a plurality of areas of the initial 3D form, a respective distance is computed from the area to a nearest one of the multiple points, and one or more of the areas for which the respective distance is greater than a specified threshold distance are identified. The initial 3D form is modified so as to bring each of the identified areas to within the specified threshold distance of at least one of the multiple points. A 3D map of the cavity is rendered to a display a based on the modified 3D form and the measured physiological data.

24 Claims, 6 Drawing Sheets

(56)          References Cited

U.S. PATENT DOCUMENTS

| | | | |
|---|---|---|---|
| 6,690,963 | B2 | 2/2004 | Ben Haim |
| 6,788,967 | B2 | 9/2004 | Ben Haim |
| 6,892,091 | B1 | 5/2005 | Ben Haim |
| 6,968,299 | B1 | 11/2005 | Bernardini |
| 7,536,218 | B2 | 5/2009 | Govari |
| 7,756,576 | B2 | 7/2010 | Levin |
| 7,848,787 | B2 | 12/2010 | Osadchy |
| 7,869,865 | B2 | 1/2011 | Govari |
| 8,456,182 | B2 | 6/2013 | Bar-Tal |
| 2013/0138404 | A1* | 5/2013 | Carbonera ........... G06T 17/205 703/2 |
| 2022/0079500 | A1 | 3/2022 | Fishel |
| 2022/0225925 | A1 | 7/2022 | Cohen |

* cited by examiner

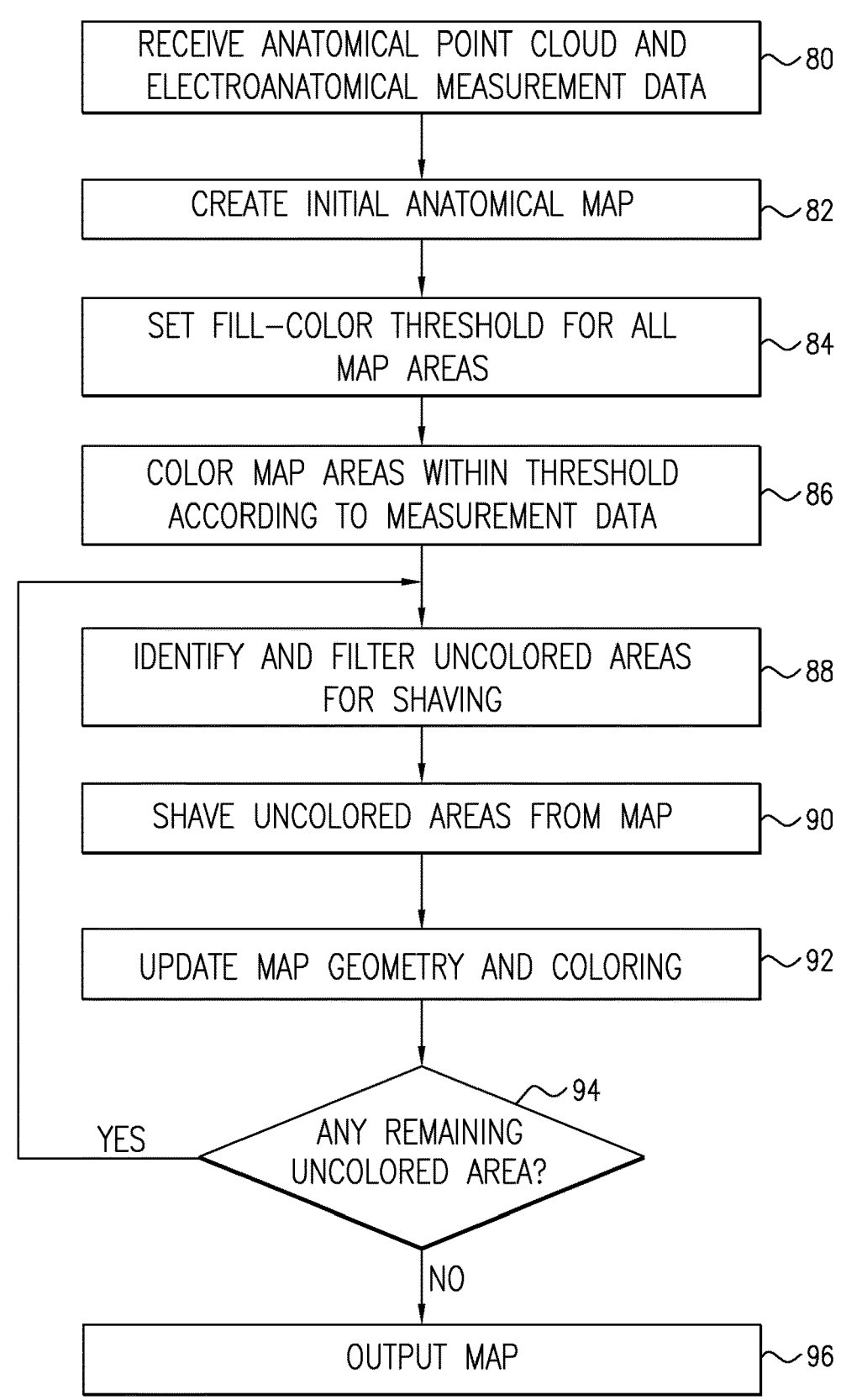

RECEIVE ANATOMICAL POINT CLOUD AND
ELECTROANATOMICAL MEASUREMENT DATA ～80

CREATE INITIAL ANATOMICAL MAP ～82

SET FILL-COLOR THRESHOLD FOR ALL
MAP AREAS ～84

COLOR MAP AREAS WITHIN THRESHOLD
ACCORDING TO MEASUREMENT DATA ～86

IDENTIFY AND FILTER UNCOLORED AREAS
FOR SHAVING ～88

SHAVE UNCOLORED AREAS FROM MAP ～90

UPDATE MAP GEOMETRY AND COLORING ～92

ANY REMAINING
UNCOLORED AREA? ～94

YES

NO

OUTPUT MAP ～96

FIG. 4

AUTOMATIC EDITING OF ELECTROANATOMICAL MAPS

FIELD

The present disclosure relates generally to graphical representation and display of anatomical structures, and particularly to electroanatomical mapping of organs, such as the heart.

BACKGROUND

In electroanatomical mapping, the three-dimensional (3D) shape of the surface of a body organ is measured and modeled as a 3D map, and electrical activity at locations along the surface is measured and displayed on the 3D map. For example, the internal shape of a chamber of the heart may be mapped by inserting a position-sensing catheter into the chamber and moving the distal end of the catheter within the chamber to generate a point cloud of position coordinates. A process of fast anatomical mapping (FAM) converts the outer surface of the point cloud into a 3D mesh representing the endocardial surface of the chamber. Electrodes on the distal end of the catheter measure electrical potentials at many points on the endocardial surface. These electrical measurements are typically represented as colors applied to the corresponding locations on the 3D mesh. The colors between the measurement points can be interpolated to visualize the electrical activity over the entire 3D surface of the heart chamber.

U.S. Patent Application Publication 2022/0225925, whose disclosure is incorporated herein by reference, describes a method that includes receiving or generating a volume map of at least a portion of a cavity of an organ of a body including a plurality of mapped locations, and a point cloud of locations in the cavity marked for treatment. The volume map is updated by removing a portion of the mapped locations, so that the locations marked for treatment fall on a surface of the volume map. Using the updated volume map, a map of at least a portion of the cavity is generated, the map including the locations marked for treatment. The map is displayed to a user.

The present disclosure will be more fully understood from the following detailed description of the examples thereof, taken together with the drawings in which:

BRIEF DESCRIPTION OF THE DRAWINGS

FIG. 4 is a flow chart that schematically illustrates a method for creating an electroanatomical map, in accordance with an example of the disclosure.

DETAILED DESCRIPTION

Overview

Figure 1:
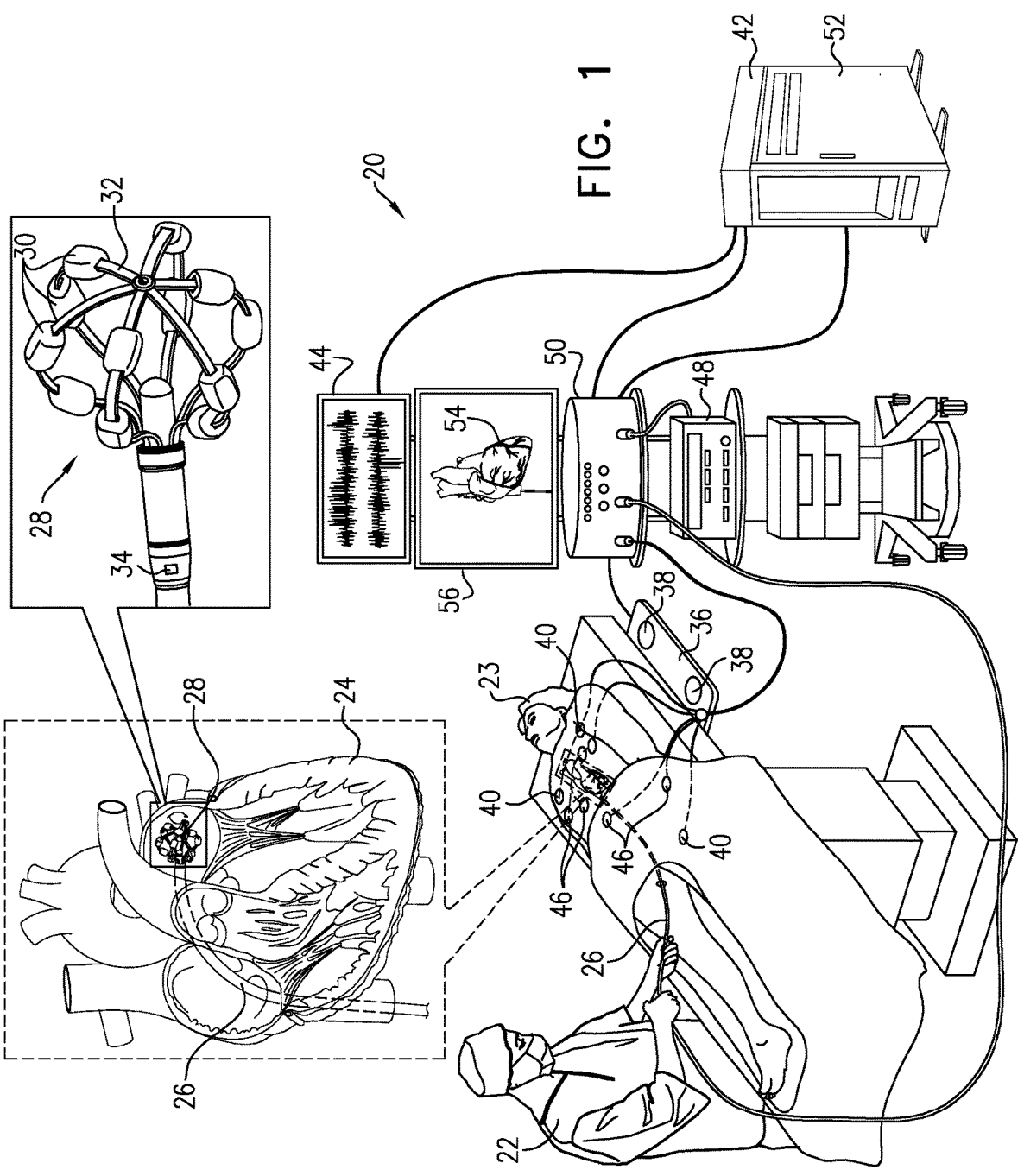
FIG. 1 is schematic pictorial illustration of a catheter-based electrophysiology mapping and ablation system, in accordance with an example of the disclosure.

When an anatomical map is created of the inner surface of a body cavity, such as the inner surface of a heart chamber, using the sort of FAM process that is described above, the surface of the map is often "inflated" relative to the actual anatomy of the cavity. In other words, parts of the surface of the 3D map extends beyond the bounds of the actual anatomical surface. One reason for this sort of inflation in a map of a heart chamber, for example, is that the locations of the points that are used in the FAM process are acquired over different periods in the cardiac and respiratory cycles, and the resulting movement of the heart wall causes smearing of the map. Another reason is "tenting": outward distortion of the inner surface of the cavity due to pressure of the probe, such as a catheter, that is used in gathering the location data for mapping.

When the surface of the 3D anatomical map is rendered to a display, physiological data measured within the cavity can be represented on the display. For example, electrophysiological measurements made by a catheter at points on the inner surface of a heart chamber can be presented by coloring the 3D map to represent local potential levels or electrical activation times. To display the measured data, each physiological measurement point is projected onto the closest area of the map. Areas of the map for which there is no nearby physiological measurement point will not display any measurement indication. For example, when colors are used to represent the physiological measurements, areas for which there is no nearby measurement point may be colored gray.

"Gray areas" of this sort can arise not only when there is a shortage of measurement points, but also due to local inflation of the 3D anatomical map, which pushes the map surface away from the actual measurement points. As a result, gray areas of a colored electroanatomical map may erroneously appear to indicate a lack of electrical activity, as well as misrepresenting the shape of the heart chamber. A cardiologist may be able to recognize and correct these areas by interaction with the computer system that is used to produce the map, but this interactive process is difficult and time-consuming.

Examples of the present disclosure address these problems by automatically identifying and correcting distortions of the 3D anatomical map. In these examples, a computer identifies the areas of the map that are distant from the nearest measurement points and "shaves" the map in these areas, i.e., it reduces the volume of the map in each area and thus brings the map surface closer to the nearest measurement point. This process of shaving can be performed iteratively, so that the map surface is gradually adjusted to the desired shape, or it can be carried out by modifying the map surface in a single step. In either case, the end result will be that the identified areas of the map surface are brought to within a small distance from the nearest measurement points and thus can be properly colored or otherwise marked to represent the measured physiological data. This process of map adjustment can be carried out automatically over the entire area of the 3D anatomical map or, alternatively, over certain selected areas.

Thus, examples of the present disclosure provide a method for mapping in which a processor computes an initial 3D form, representing an inner surface of a cavity within a body of a living subject. The processor also receives physiological data measured at multiple points distributed over the inner surface of the cavity. In the examples that are described below, the 3D form is assumed to be an anatomical map of a heart chamber, derived from a point cloud collected by a catheter using a FAM algorithm; and the physiological data are based on electrical measurements made on the endocardial surface of the heart chamber. Alternatively, the principles of the present disclosure may be applied to other body cavities and mapping techniques, as well as to other sorts of physiological data.

For some or all areas of the initial 3D form, the processor computes a respective distance from the area to a nearest measurement point and thus identifies any areas for which the respective distance is greater than a specified threshold distance. Assuming map coloring is used to represent the physiological data, these areas would be colored gray. The processor modifies the initial 3D form so as to bring each of these identified areas to within the specified threshold distance of at least one of the multiple points. The processor then renders to a display a 3D map of the cavity based on the modified 3D form and the measured physiological data.

System Description

FIG. 1 shows an example catheter-based electrophysiology mapping and ablation system 20. System 20 may include multiple catheters, which are percutaneously inserted by a physician 22 through the vascular system of a patient 23 into a chamber or vascular structure of a heart 24. Typically, a delivery sheath (not shown) is inserted into the left or right atrium near a desired location in heart 24. Thereafter, one or more catheters 26 are inserted through the delivery sheath so as to arrive at the desired location in heart 24. The multiple catheters may include catheters dedicated for sensing intracardiac electrogram (IEGM) signals, catheters dedicated for ablating, and/or catheters used for both sensing and ablating.

The distal part of catheter 26 in the pictured example comprises a basket assembly 28. Physician 22 may manipulate catheter 26 to place basket assembly 28 in contact with the heart wall for sensing a target site in heart 24 and/or for ablating tissue at the target site. Alternatively, catheter 26 may comprise other sorts of distal assemblies, such as multiple flexible arms, a helical "lasso," or simply a linear distal section.

Catheter 26 is an exemplary catheter that includes multiple electrodes 30 distributed over a plurality of spines 32 in basket assembly 28 and configured to sense IEGM signals and/or ablate myocardial tissue. Catheter 26 additionally includes one or more position sensors 34 embedded in the distal part of the catheter for tracking the position and orientation of basket assembly 28, as described further hereinbelow. For example, position sensor 34 may comprise a magnetic position sensor including three magnetic coils for sensing three-dimensional (3D) position and orientation.

Magnetic position sensor 34 may be operated together with a location pad 36 including multiple magnetic coils 38 configured to generate magnetic fields in a predefined working volume containing heart 24. The position of basket assembly 28 of catheter 26 may be tracked based on magnetic fields generated by location pad 36 and sensed by magnetic position sensor 34. Details of magnetic position sensing technology that may be applied for this purpose are described, for example, in U.S. Pat. Nos. 5,539,199; 5,443,489; 5,558,091; 6,172,499; 6,239,724; 6,332,089; 6,484,118; 6,618,612; 6,690,963; 6,788,967; and 6,892,091.

System 20 optionally includes one or more electrode patches 40 in contact with the skin of patient 23 to establish location references for location pad 36, as well as for impedance-based tracking of electrodes 30. For impedance-based tracking, electrical current is directed to electrodes 30 and sensed at electrode patches 40 so that the location of each electrode 30 can be triangulated via electrode patches 40. Details of this sort of impedance-based location tracking technology are described in U.S. Pat. Nos. 7,536,218; 7,756,576; 7,848,787; 7,869,865; and 8,456,182.

A recorder 42 records and displays electrograms 44 captured by body-surface ECG electrodes 46 and intracardiac electrograms (IEGM) captured by electrodes 30 of catheter 26. Recorder 42 may include pacing capability for pacing the heart rhythm and/or may be electrically connected to a standalone pacer.

System 20 may include an ablation energy generator 48 for providing ablative energy to one or more of electrodes 30. Energy produced by ablation energy generator 48 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

A patient interface unit (PIU) 50 comprises an interface for electrical communication between catheters 26, other electrophysiological equipment, a power supply, and a computer workstation 52 for controlling operation of system 20. Electrophysiological equipment in system 20 may include for example, multiple catheters 26, location pad 36, body surface ECG electrodes 46, electrode patches 40, ablation energy generator 48, and recorder 42. Optionally, PIU 50 additionally includes processing capability for implementing real-time computations of the position of the catheters and for processing ECG signals.

Workstation 52 includes a memory and a processor, with appropriate operating software stored in the memory, including software for carrying out the mapping functions that are described herein, and user interface capability. The software may be stored on tangible, non-transitory computer-readable media, such as optical, magnetic, or electronic memory media. Workstation 52 may provide multiple functions, optionally including (1) modeling the endocardial anatomy in three-dimensions (3D) and rendering the model or an anatomical map 54 for display on a display device 56; (2) displaying on display device 56 activation sequences (or other data) compiled from recorded electrograms 44 in representative visual indicia or imagery superimposed on the rendered anatomical map 54; (3) displaying real-time location and orientation of one or more catheters within heart 24; and (4) displaying on display device 56 sites of interest such as places where ablation energy has been applied. A commercial product embodying elements of system 20 is the CARTO® 3 System, available from Biosense Webster, Inc. (31A Technology Drive, Irvine, CA 92618).

Methods of Mapping

For the sake of convenience and clarity, methods for the generation and display of electroanatomical maps will be described hereinbelow with specific reference to catheter 26, workstation 52, and other elements of system 20, as shown in FIG. 1. Alternatively, the principles of the present disclosure may be applied using data acquired by other sorts of probes and systems and may also be applied to other organs and cavities in the body, as well as other types of physiological data.

Figure 2:
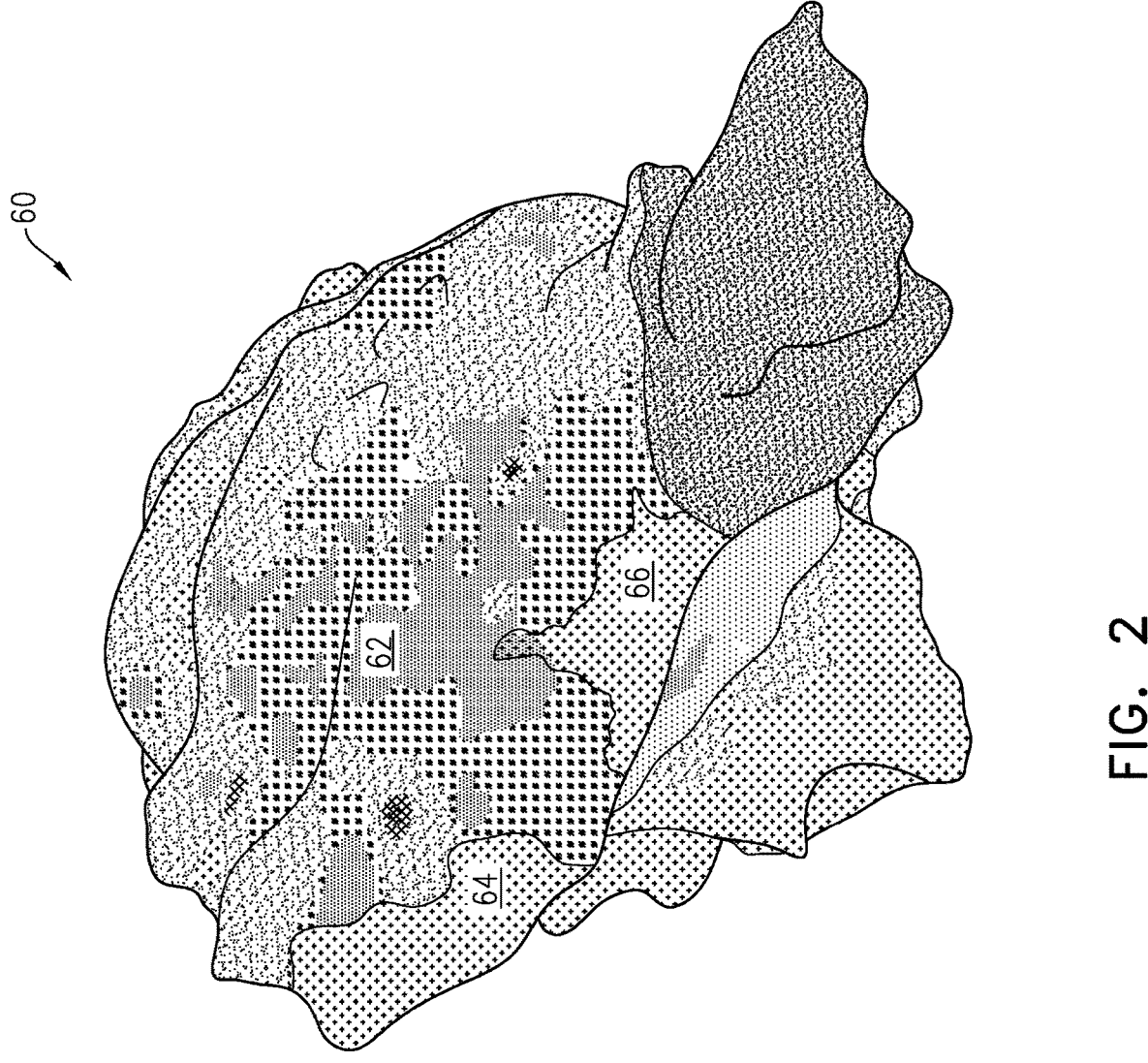
FIG. 2 is a schematic pictorial representation of an electroanatomical map, in accordance with an example of the disclosure.

FIG. 2 is a schematic pictorial representation of an initial electroanatomical map 60 of a heart chamber, in accordance with an example of the disclosure. As explained above, a processor, such as the processor in workstation 52, creates map 60 based on information provided by catheter 26 via PIU 50. This information includes location coordinates and electrical signals acquired while basket assembly 28 (or another sort of distal assembly on catheter 26) moves within the heart chamber.

An outer surface 62 of map 60 corresponds to the estimated shape of the endocardial surface of the heart chamber. Surface 62 comprises a polygonal mesh, for example a triangular mesh, which is created by a technique such as Fast Anatomical Mapping (FAM) and contains the extent of the movements of the distal part of the catheter within the heart. In other words, surface 62 bounds a volume of the point cloud within which, but not outside of which, the distal part of the catheter was moved. Surface 62 may be reconstructed, for example, using a ball-pivoting algorithm, as described in U.S. Pat. No. 6,968,299, or using any other suitable method of surface reconstruction that is known in the art. Map 60 represents the initial 3D form computed by workstation 52 based on the acquired point cloud, prior to the process of "shaving" that is described below.

Surface 62 is colored on display device 56 to represent the physiological data measured at different points on the endocardial surface. In the present example, the physiological data are assumed to comprise electrical data, and the colors of different areas on the surface represent the local values of electrophysiological parameters, such as the unipolar voltage or the local activation time (LAT). Each area of surface 62 is colored according to value of the electrical data measured at the point that is nearest to the area. The colors may be interpolated to give smooth transitions.

Areas 64 and 66 in FIG. 2, however, are colored gray, meaning that the nearest electrical measurement point to each of these areas was more than a certain threshold distance away. As explained earlier, these gray areas may arise do to "inflation" of the point cloud used in the FAM algorithm relative to the actual endocardial surface. The threshold distance for coloring may be fixed, either automatically or by a user of system 20, or it may be determined adaptively, for example based on statistics of the data acquired from catheter 26.

Figure 3:
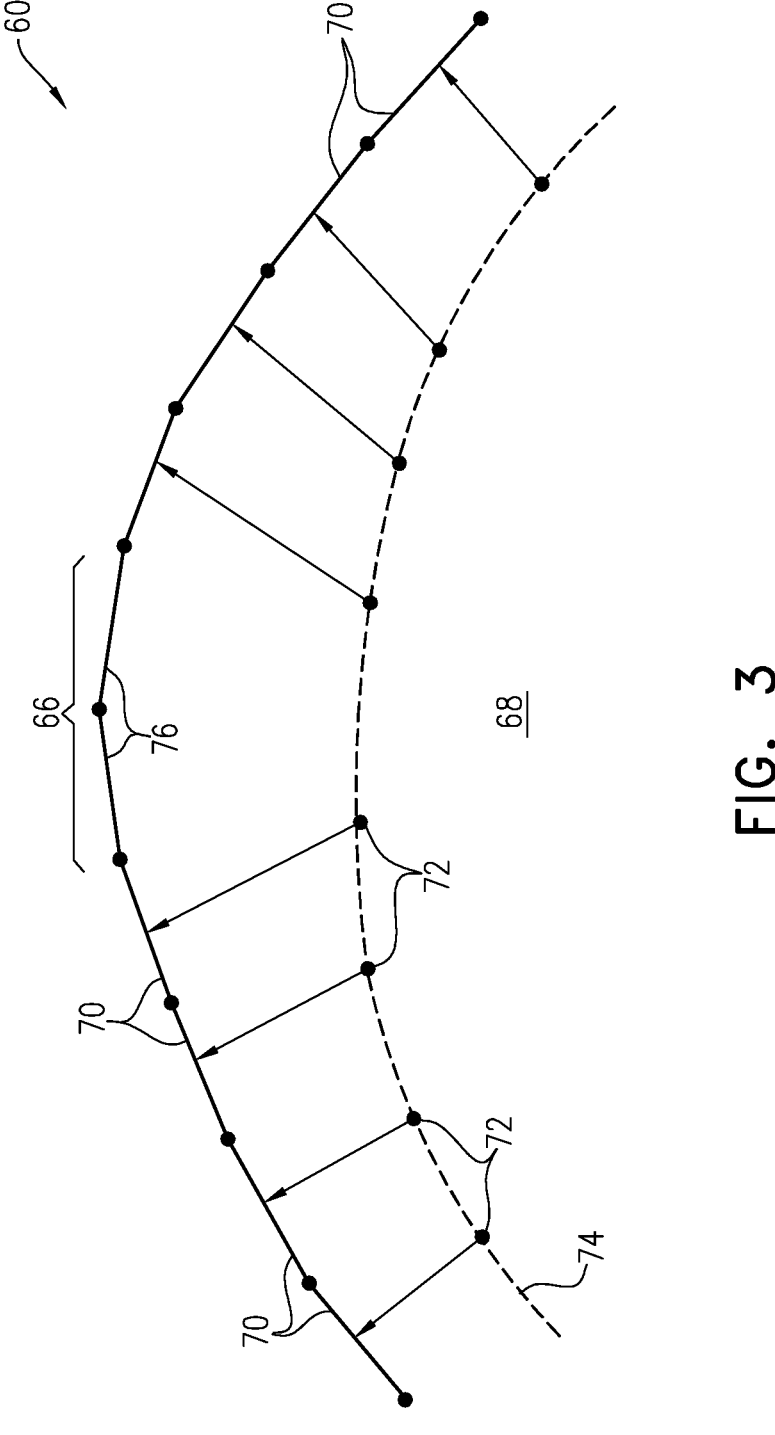
FIG. 3 is a schematic sectional view of an anatomical map illustrating a method for applying electrical data to the map, in accordance with an example of the disclosure.

FIG. 3 is a schematic sectional view of electroanatomical map 60, illustrating a method for applying electrical data to the map, in accordance with an example of the disclosure. System 20 has acquired electrical data at a set of measurement points 72 distributed over a myocardial surface 74 of a heart chamber 68. Each point 72 is projected onto the nearest one of a set of triangles 70 (or other polygons), which make up the mesh created from the point cloud using the FAM algorithm. In area 66, however, triangles 76 are spaced away from surface 74, and thus from the nearest measurement points 72, by more than the threshold distance. Therefore, given the initial 3D form of map 60, triangles 76 are not colored and remain gray.

FIG. 4 is a flow chart that schematically illustrates a method for creating an electroanatomical map, in accordance with an example of the disclosure. The method begins with receiving an anatomical point cloud of location points acquired within a heart chamber, as well as electrical measurements made at points on the endocardial surface of the heart chamber, at a data acquisition step 80. The location points and electrical data may be acquired in real time by workstation 52 from catheter 26, or they may be stored in a memory and read out at a later time by a computer implementing this method. In either case, workstation 52 creates an initial anatomical map, for example by applying a FAM process to the point cloud generated by catheter 26, at a map creation step 82. As noted earlier, the anatomical map typically has the form of a triangular mesh (or other polygonal mesh).

Workstation 52 sets a fill-color threshold for all areas of the initial anatomical map, at a threshold setting step 84. As noted earlier, the threshold represents a maximum permitted distance between measurement points 72 and triangles 70 (FIG. 3) and may be fixed or vary adaptively over the area of the map. Workstation 52 measures the distance from each triangle 70 to the nearest measurement point 72, at a coloring step 86. Triangles that are within the threshold distance of the nearest measurement points are colored according to the values of the electrophysiological parameters measured at the corresponding points. Triangles 76, which are beyond the threshold distance, remain uncolored.

The distance measured at step 86 may be defined in various ways. For example, workstation 52 may measure the respective geodesic distance of each vertex of the mesh from the nearest measurement point. When all the vertices of a given triangle are beyond the threshold distance, the triangle remains uncolored. When all the vertices are within the threshold distance, the triangle is colored. When one or two vertices of a given triangle are beyond the threshold distance, while the other vertex or vertices are within the threshold distance, workstation may split the triangle into nearer and farther parts and then color only the nearer part.

After the initial map has been colored, workstation 52 identifies the areas of the map that have not been colored, at a gray identification step 88. The workstation reviews this collection of gray areas to filter out areas that should not be shaved, for example because they represent anatomical features or otherwise to avoid removing too much of the volume of the initial map. Workstation 52 then shaves a certain volume of the initial map below each of the uncolored triangles, at a shaving step 90 (other than in areas that were filtered out of the shaving operation at step 88). For the purpose of shaving, workstation 52 may compute a volume of the point cloud falling inside the initial map surface to a specified depth beneath each uncolored triangle, for example to a depth of 2 mm, and may then erase the part of the point cloud within this volume.

After the volumes beneath the uncolored triangles have been shaved, workstation 52 reconstructs the triangular mesh, at least in the vicinity of the areas that have been shaved, at a map geometry update step 92. This reconstruction can use the same FAM algorithm as was used in step 82 but will now result in a reduced volume of the anatomical map in the uncolored areas. In the areas of the map that have been shaved, workstation 52 repeats the measurements of distance from the triangles to the nearest measurement points and appropriately colors the triangles that are now within the threshold distance.

After completing the updates at step 92, workstation 52 checks whether any areas of the map remain uncolored (other than areas that were filtered out of the shaving process), at a completion checking step 94. If so, workstation 52 repeats steps 88, 90 and 92 over these uncolored areas. In repeating step 90, workstation will iteratively remove further volumes beneath the uncolored triangles that remain in the modified triangular mesh that was created by the previous pass through steps 90 and 92. These iterations will typically continue until all the remaining uncolored triangles have been brought within the threshold distance of the nearest measurement points and are colored accordingly. When workstation 52 finds at step 94 that this iterative process has been completed, the workstation outputs the final, fully colored 3D map, for example by rendering the map to display device 56.

Figure 5:
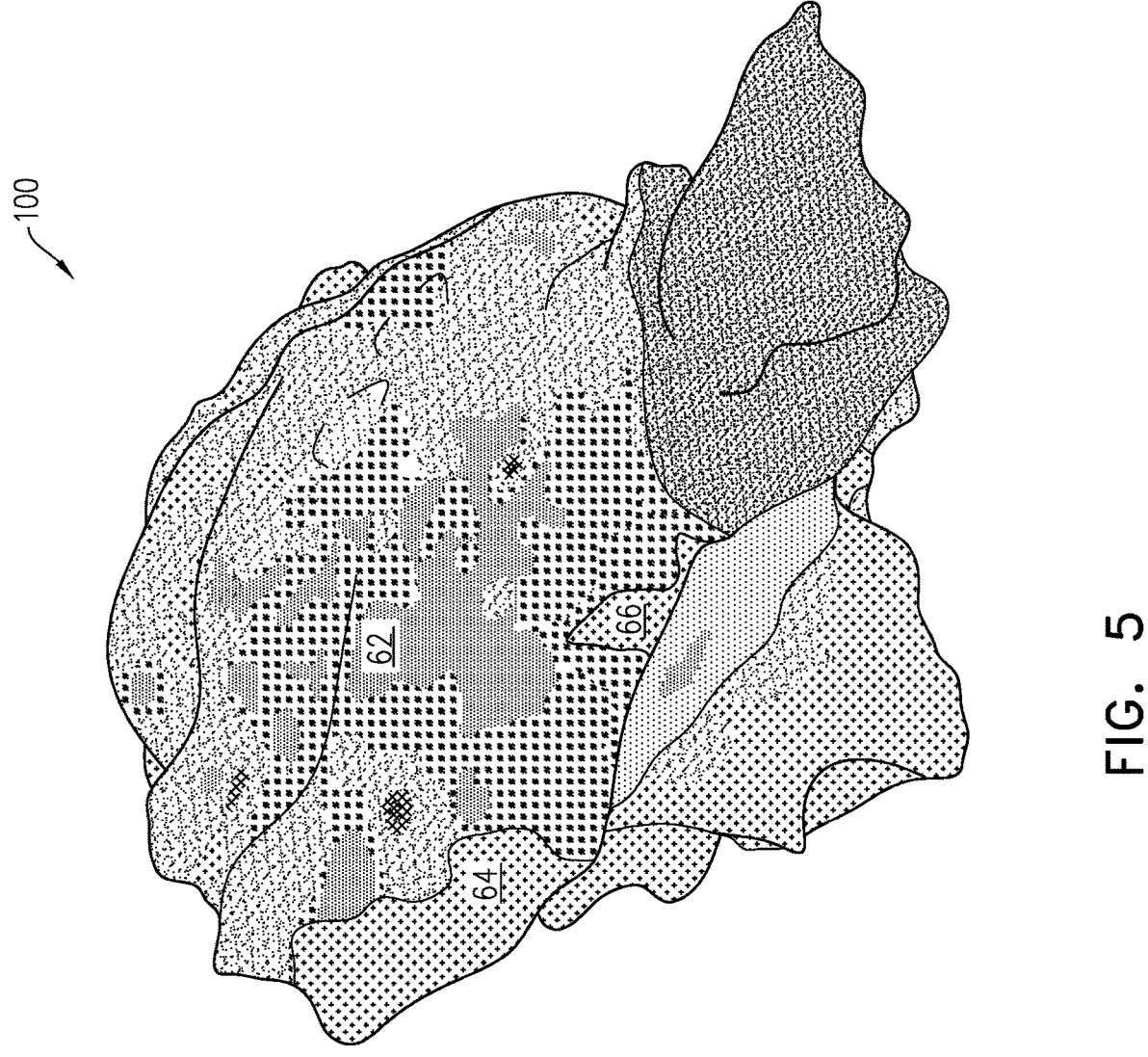
FIGS. 5 and 6 are schematic pictorial representations of an electroanatomical map in successive stages of modification of the map surface, in accordance with an example of the disclosure.
Figure 6:
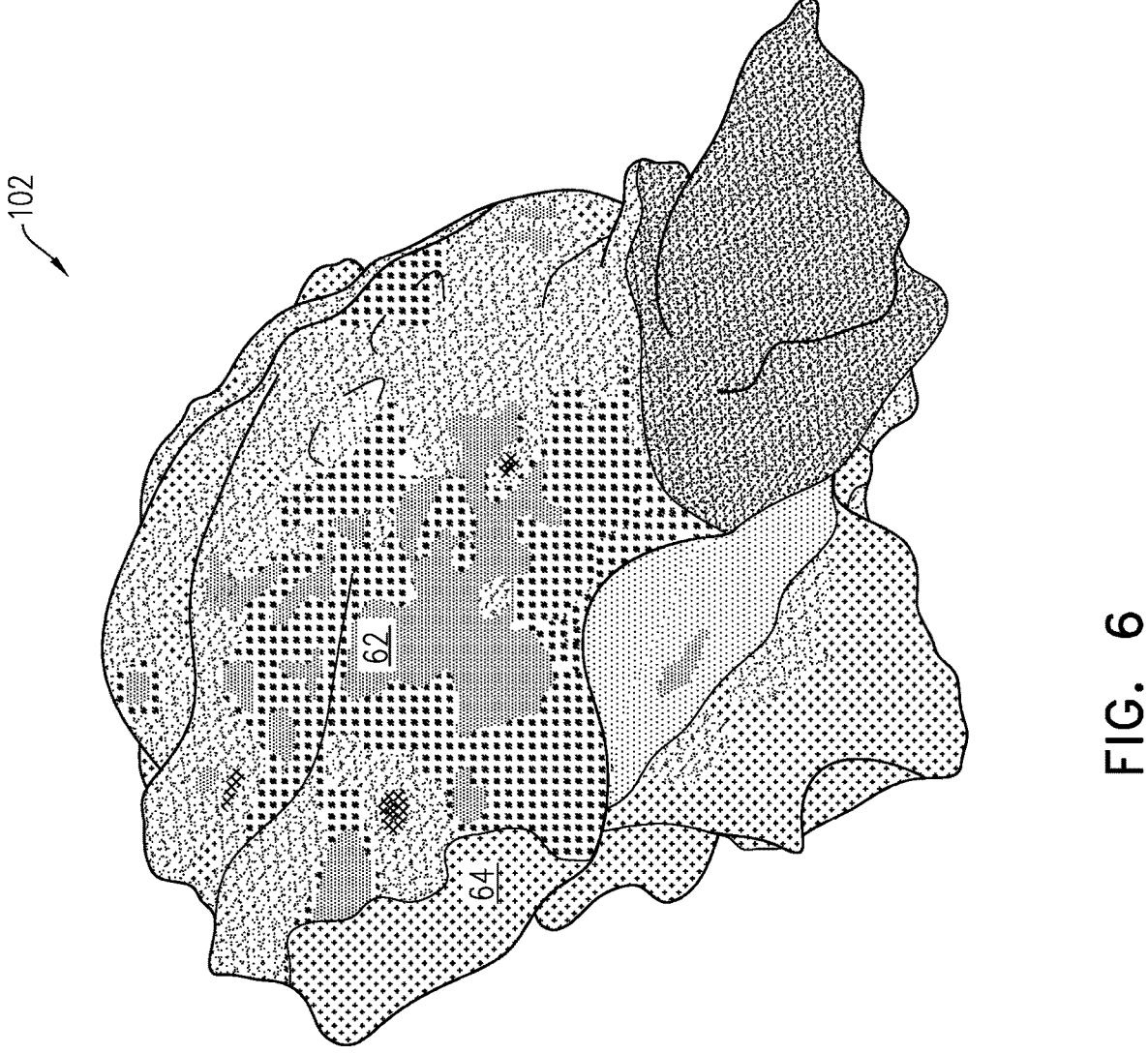

FIGS. 5 and 6 are schematic pictorial representations of electroanatomical maps 100, 102 in successive stages of modification of the map surface, in accordance with an example of the disclosure. In map 100, the large gray area 66 in map 60 (FIG. 2) has been reduced in size by a first shaving iteration. In map 102, area 66 has been eliminated by further shaving, and this part of the map is entirely colored. (Gray area 64 has not yet been shaved in this example.)

EXAMPLES

Example 1: A method for mapping comprises computing an initial three-dimensional (3D) form representing an inner surface of a cavity within a body of a living subject (23), receiving physiological data measured at multiple points distributed over the inner surface of the cavity, for each area (70, 76) among a plurality of areas of the initial 3D form, computing a respective distance from the area to a nearest one of the multiple points, identifying one or more of the areas for which the respective distance is greater than a specified threshold distance, modifying the initial 3D form so as to bring each of the identified areas to within the specified threshold distance of at least one of the multiple points, and rendering to a display (56) a 3D map (102) of the cavity based on the modified 3D form and the measured physiological data.

Example 2: The method according to example 1, wherein computing the initial 3D form comprises receiving a point cloud comprising multiple location coordinates of a probe acquired while the probe moved within the cavity, and modeling an outer surface of the point cloud to find the initial 3D form of the inner surface of the cavity.

Example 3: The method according to example 1 or 2, wherein computing the initial 3D form comprises constructing a polygonal mesh representing the inner surface of the cavity, and wherein computing the respective distance comprises finding the respective distance from each polygon within the mesh to the nearest one of the multiple points.

Example 4: The method according to example 3, wherein identifying one or more of the areas comprises identifying a polygon for which the respective distance to the respective one of the multiple points is greater than the specified threshold, and wherein modifying the initial 3D form comprises removing a volume of the initial 3D form that is contained within a specified depth beneath the identified polygon, and reconstructing the polygonal mesh in a vicinity of the removed volume.

Example 5: The method according to example 4, and comprising, after reconstructing the polygonal mesh, recomputing the respective distance from the polygon to the nearest one of the multiple points and, when the recomputed distance is still greater than the specified threshold, iteratively removing one or more further volumes beneath the modified polygonal mesh until the recomputed distance is no greater than the specified threshold.

Example 6: The method according to any of examples 3-5, wherein constructing the polygonal mesh comprises constructing a triangular mesh, and wherein finding the respective distance comprises measuring a geodesic distance from each vertex of each triangle in the mesh to a respective one of the multiple points that is nearest to the vertex.

Example 7: The method according to any of the preceding examples, wherein receiving the physiological data comprises receiving electrophysiological data acquired at the multiple points by a probe within the cavity.

Example 8: The method according to example 7, wherein receiving the electrophysiological data comprises receiving electrical signals measured by a catheter within a chamber of a heart of the living subject, and wherein rendering the 3D map comprises producing an electroanatomical map of the chamber.

Example 9: The method according to any of the preceding examples, wherein rendering the 3D map comprises coloring the areas of the modified 3D form that is presented on the display according to values of the physiological data measured at the points that are nearest to the areas.

Example 10. A system (20) for mapping comprises an interface (50) configured to receive physiological data measured at multiple points distributed over the inner surface of a cavity within a body of a living subject (23) and a processor (52) configured to compute an initial three-dimensional (3D) form representing an inner surface of the cavity, and to compute, for each area (70, 76) among a plurality of areas of the initial 3D form, a respective distance from the area to a nearest one of the multiple points, to identify one or more of the areas for which the respective distance is greater than a specified threshold distance, to modify the initial 3D form so as to bring each of the identified areas to within the specified threshold distance of at least one of the multiple points, and to render to a display (56) a 3D map (102) of the cavity based on the modified 3D form and the measured physiological data.

Example 11. A computer software product, comprising a tangible, non-transitory computer-readable medium in which program instructions are stored, which instructions, when read by a computer (52), cause the computer to receive physiological data measured at multiple points distributed over the inner surface of a cavity within a body of a living subject, to compute an initial three-dimensional (3D) form representing an inner surface of the cavity, and to compute, for each area (70, 76) among a plurality of areas of the initial 3D form, a respective distance from the area to a nearest one of the multiple points, to identify one or more of the areas for which the respective distance is greater than a specified threshold distance, to modify the initial 3D form so as to bring each of the identified areas to within the specified threshold distance of at least one of the multiple points, and to render to a display (56) a 3D map (102) of the cavity based on the modified 3D form and the measured physiological data.

The implementations described above are cited by way of example, and the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing description and which are not disclosed in the prior art.

The invention claimed is:

1. A method for mapping, comprising:

computing an initial three-dimensional (3D) form representing an inner surface of a cavity within a body of a living subject;

measuring electrophysiological data at multiple points distributed over the inner surface of the cavity using a probe within the cavity;

for each area among a plurality of areas of the initial 3D form, computing a respective distance from the area to a nearest one of the multiple points;

identifying one or more of the areas for which the respective distance is greater than a specified threshold distance;

shaving the initial 3D form so as to bring each of the identified areas to within the specified threshold distance of at least one of the multiple points; and displaying a 3D map of the cavity based on the shaved 3D form and the measured electrophysiological data.

2. The method according to claim 1, wherein computing the initial 3D form comprises receiving a point cloud comprising multiple location coordinates of the probe acquired while the probe moved within the cavity, and modeling an outer surface of the point cloud to find the initial 3D form of the inner surface of the cavity.

3. The method according to claim 1, wherein computing the initial 3D form comprises constructing a polygonal mesh representing the inner surface of the cavity, and wherein computing the respective distance comprises finding the respective distance from each polygon within the mesh to the nearest one of the multiple points.

4. The method according to claim 3, wherein identifying one or more of the areas comprises identifying a polygon for which the respective distance to the respective one of the multiple points is greater than the specified threshold, and wherein shaving the initial 3D form comprises removing a volume of the initial 3D form that is contained within a specified depth beneath the identified polygon, and reconstructing the polygonal mesh in a vicinity of the removed volume.

5. The method according to claim 4, and comprising, after reconstructing the polygonal mesh, recomputing the respective distance from the polygon to the nearest one of the multiple points and, when the recomputed distance is still greater than the specified threshold, iteratively removing one or more further volumes beneath the reconstructed polygonal mesh until the recomputed distance is no greater than the specified threshold.

6. The method according to claim 3, wherein constructing the polygonal mesh comprises constructing a triangular mesh, and wherein finding the respective distance comprises measuring a geodesic distance from each vertex of each triangle in the mesh to a respective one of the multiple points that is nearest to the vertex.

7. The method according to claim 1, wherein measuring the electrophysiological data comprises measuring electrical signals using a catheter within a chamber of a heart of the living subject, and wherein displaying the 3D map comprises displaying an electroanatomical map of the chamber.

8. The method according to claim 1, wherein displaying the 3D map comprises coloring the areas of the shaved 3D form according to values of the electrophysiological data measured at the points that are nearest to the areas.

9. A system for mapping, comprising:

a probe that measures electrophysiological data at multiple points distributed over an inner surface of a cavity within a body of a living subject;

an interface configured to receive the electrophysiological data measured at the multiple points distributed over the inner surface of the cavity; and a processor configured to:

compute an initial three-dimensional (3D) form representing the inner surface of the cavity;

compute, for each area among a plurality of areas of the initial 3D form, a respective distance from the area to a nearest one of the multiple points;

identify one or more of the areas for which the respective distance is greater than a specified threshold distance;

shave the initial 3D form so as to bring each of the identified areas to within the specified threshold distance of at least one of the multiple points; and display a 3D map of the cavity based on the shaved 3D form and the measured electrophysiological data.

10. The system according to claim 9, wherein the processor is configured to receive a point cloud comprising multiple location coordinates of the probe acquired while the probe moved within the cavity, and to model an outer surface of the point cloud to find the initial 3D form of the inner surface of the cavity.

11. The system according to claim 9, wherein the initial 3D form comprises a polygonal mesh representing the inner surface of the cavity, and wherein the processor is configured to compute the respective distance from each polygon within the mesh to the nearest one of the multiple points.

12. The system according to claim 11, wherein the processor is configured to identify a polygon for which the respective distance to the respective one of the multiple points is greater than the specified threshold, and to shave the initial 3D form by removing a volume of the initial 3D form that is contained within a specified depth beneath the identified polygon, and reconstructing the polygonal mesh in a vicinity of the removed volume.

13. The system according to claim 12, wherein the processor is configured, after reconstructing the polygonal mesh, to recompute the respective distance from the polygon to the nearest one of the multiple points and, when the recomputed distance is still greater than the specified threshold, to remove iteratively one or more further volumes beneath the reconstructed polygonal mesh until the recomputed distance is no greater than the specified threshold.

14. The system according to claim 11, wherein the polygonal mesh comprises a triangular mesh, and wherein the processor is configured to compute respective distances by measuring a geodesic distance from each vertex of each triangle in the mesh to a respective one of the multiple points that is nearest to the vertex.

15. The system according to claim 9, and comprising a catheter, which is configured to provide the electrophysiological data by measuring electrical signals within a chamber of a heart of the living subject, and wherein the 3D map comprises an electroanatomical map of the chamber.

16. The system according to claim 9, wherein the display of the 3D map of the cavity comprises coloring the areas of the shaved 3D form according to values of the electrophysiological data measured at the points that are nearest to the areas.

17. A computer software product, comprising a tangible, non-transitory computer-readable medium in which program instructions are stored, which instructions, when read by a computer, cause the computer to:

measure electrophysiological data at multiple points distributed over an inner surface of a cavity within a body of a living subject using a probe within the cavity;

compute an initial three-dimensional (3D) form representing an inner surface of the cavity;

compute, for each area among a plurality of areas of the initial 3D form, a respective distance from the area to a nearest one of the multiple points;

identify one or more of the areas for which the respective distance is greater than a specified threshold distance;

shave the initial 3D form so as to bring each of the identified areas to within the specified threshold distance of at least one of the multiple points; and display a 3D map of the cavity based on the shaved 3D form and the measured electrophysiological data.

18. The product according to claim 17, wherein the instructions cause the computer to receive a point cloud comprising multiple location coordinates of the probe acquired while the probe moved within the cavity, and to model an outer surface of the point cloud to find the initial 3D form of the inner surface of the cavity.

19. The product according to claim 17, wherein the initial 3D form comprises a polygonal mesh representing the inner surface of the cavity, and wherein the instructions cause the computer to compute the respective distance from each polygon within the mesh to the nearest one of the multiple points.

20. The product according to claim 19, wherein the instructions cause the computer to identify a polygon for which the respective distance to the respective one of the multiple points is greater than the specified threshold, and to shave the initial 3D form by removing a volume of the initial 3D form that is contained within a specified depth beneath the identified polygon, and reconstructing the polygonal mesh in a vicinity of the removed volume.

21. The product according to claim 20, wherein the instructions cause the computer, after reconstructing the polygonal mesh, to recompute the respective distance from the polygon to the nearest one of the multiple points and, when the recomputed distance is still greater than the specified threshold, to remove iteratively one or more further volumes beneath the reconstructed polygonal mesh until the recomputed distance is no greater than the specified threshold.

22. The product according to claim 19, wherein the polygonal mesh comprises a triangular mesh, and wherein the instructions cause the computer to compute respective distances by measuring a geodesic distance from each vertex of each triangle in the mesh to a respective one of the multiple points that is nearest to the vertex.

23. The product according to claim 17, wherein the instructions cause the computer to:

acquire the electrophysiological data from electrical signals measured using a catheter within a chamber of a heart of the living subject; and display an electroanatomical map of the chamber using the electrophysiological data.

24. The product according to claim 17, wherein the display of the 3D map of the cavity comprises coloring the areas of the shaved 3D form according to values of the electrophysiological data measured at the points that are nearest to the areas.

* * * * *